United States Patent [19]

Parrinello

[11] Patent Number: 5,707,996
[45] Date of Patent: Jan. 13, 1998

[54] PHARMACEUTICAL SOLUTION AND METHODS FOR PREPARATION THEREOF

[75] Inventor: Giovanni Parrinello, Fort Collins, Colo.

[73] Assignee: Macleod Pharmaceuticals, Inc., Fort Collins, Colo.

[21] Appl. No.: 554,041

[22] Filed: Nov. 6, 1995

[51] Int. Cl.$^6$ .................................................. A61K 31/505
[52] U.S. Cl. ............................................... 514/256
[58] Field of Search ................................. 514/385, 256

[56] References Cited

U.S. PATENT DOCUMENTS

| | | |
|---|---|---|
| 4,332,796 | 6/1982 | Los . |
| 4,386,084 | 5/1983 | Scharwaechter et al. . |
| 4,415,574 | 11/1983 | Laruelle et al. . |
| 4,532,245 | 7/1985 | Kompis . |
| 4,587,341 | 5/1986 | Roth et al. . |
| 4,587,342 | 5/1986 | Daluge et al. . |
| 4,705,803 | 11/1987 | Kern et al. . |
| 4,772,460 | 9/1988 | Malook et al. . |
| 4,795,639 | 1/1989 | Burchall et al. . |
| 4,996,198 | 2/1991 | Schildknecht et al. . |
| 5,063,219 | 11/1991 | Schildknecht et al. . |

OTHER PUBLICATIONS

*Review of Excipients and pH's for Parenteral Products Used in the United States*, Yu–Chang John Wang and Robert R. Kowal, Journal of Parenteral Drug Association, published Sep. 3, 1980, pp. 452–462.

*The Theory and Practice of Industrial Pharmacy*, Leon Lachman, Ph.D., Herbert A. Lieberman, Ph.D., Joseph L. Kanig, Ph.D., Third Edition, Lea & Febiger—1986—Philadelphia, pp. 642–644.

*Veterinary Pharmaceuticals & Biologicals*, 1982/1983, Editor: Dr. Carl E. Aronson. Consulting Editors: Thomas E. Porness, Samuel F. Scheidy, Veterinary Medicine Publishing Co., pp. 16/313–16/315, Jan., 1983.

*Use of Nonaqueous Solvents in Parenteral Products*, by A. J. Spiegel and M. M. Noseworthy, Journal of Pharmaceutical Sciences, Oct. 1963, vol. 52, No. 10.

*Serum Concentrations of Trimethoprim and Sulfadiazine Following Oral Paste Administration to teh Horse*, C.W. Sigel, Ph.D.; T.D. Byars, DVM; T. J. Divers, DVM; O. Murch, DVSC and D. DeAngelis, AB—AM J Vet Res, vol. 42, No. 11, Nov. 1982, pp. 2002–2005.

*Trimethoprim–sulfadiazine in the horse: Serum, synovial, peritoneal and urine concentrations after single–dose intravenous administration*, Murray P. Brown, DVM, MS; Robin H. Kelly, BS; Susan M. Stover, DVM; Ronald Gronwall, DVM, Ph.D.—AM J Vet Res., vol. 44, No. 4, Apr. 1983 (4 pages).

*Trimethoprim/Sulfadiazine in Equine Medicine: Pharmacology and Clinical Experience in Europe*, Geoff White, MRCVS, VETMB, Proceedings of a Symposium on Trimethoprim/Sulfadiazine Clinical Application, Equine Medicine, Jan. 1984, pp. 7–13.

*Proceedings of a Symposium on Trimethoprim/Sulfadiazine*, Jan. 31, 1978, pp. 1–63.

*Primary Examiner*—Zohreh Fay
*Attorney, Agent, or Firm*—Merchant,Gould,Smith, Edell, Welter & Schmidt

[57] ABSTRACT

A liquid pharmaceutical solution having antimicrobial agent (s), an organic solvent, and an acidic or basic aqueous medium therein. Most preferred solutions include trimethoprim, sodium hydroxide, sulfadiazine, N-methylpyrrolidone and water. The present invention is also directed toward making these solutions. A most preferred composition includes: trimethoprim in an amount of about 40 mg/ml of liquid pharmaceutical solution; sulfadiazine in an amount of about 200 mg/ml of liquid pharmaceutical solution; N-methylpyrrolidone in an amount of about 514 mg/ml of liquid pharmaceutical solution, sodium hydroxide in an amount of about 30 mg/ml of liquid pharmaceutical solution and water. Methods of making the pharmaceutical solution preferably include combining the following in any order: trimethoprim, N-methylpyrrolidone, sulfadiazine, and an acidic or basic aqueous medium. Other additives, such as antioxidants and preservatives, can also be added to the liquid pharmaceutical solution.

10 Claims, No Drawings

1

PHARMACEUTICAL SOLUTION AND METHODS FOR PREPARATION THEREOF

BACKGROUND OF THE INVENTION

The present invention relates to a liquid pharmaceutical solution and methods for making. In particular, embodiments of the invention are directed toward a liquid pharmaceutical solution having a substituted pyrimidine, a sulfonamide, water, an aqueous mineral acid or hydroxide and an organic solvent therein. Preferred embodiments of the invention include trimethoprim, sulfadiazine, water, sodium hydroxide, and an organic solvent such as N-methylpyrrolidone and/or 2-pyrrolidone. The invention is also directed towards methods of making and using the solution.

Trimethoprim (i.e., 5-[(3,4,5-trimethoxyphenyl)methyl]-2,4-pyrimidinediamine or 2,4-diamino-5-(3,4,5-trimethoxybenzyl)pyrimidine) is an antimicrobial agent, which acts by inhibiting folate coenzyme synthesis in living cells. Folate coenzyme synthesis is essential to production of particular nucleic acids, which are building blocks of living organisms.

Trimethoprim acts, generally, by inhibiting an enzyme that facilitates the conversion of dihydrofolic acid to tetrahydrofolic acid. Typically, trimethoprim has a high selectivity for inhibiting folate synthesis in protozoal enzymes. This high selectivity decreases the tendency for trimethoprim to inhibit folate coenzyme synthesis in host cells. Because trimethoprim tends not to interfere with host cell folate coenzyme synthesis, it is frequently used in antimicrobial and pharmaceutical compositions for animals.

It is known that when trimethoprim is combined with an active sulfonamide, such as sulfadiazine, a synergistic antimicrobial activity is obtained. This antimicrobial activity is effective against gram-positive and gram-negative bacterial pathogens. Thus, compositions containing trimethoprim and sulfonamides, such as sulfadiazine, have a broad spectrum of activity against a wide range of gram-positive and gram-negative bacterial pathogens.

Trimethoprim is generally not soluble in water (i.e., the solubility at room temperature is about 0.04 g/100 ml). Thus, the use of trimethoprim and a sulfonamide in an injectable pharmaceutical composition is usually restricted to those applications that allow for injection of a suspension. Particular precautions are typically taken when a suspension is injected. The person injecting the composition usually injects more slowly and carefully in order not to clog the needle with precipitated clumps in the suspension and harm the host. These clumps tend not to readily dissolve once injected into the animal. Thus, injecting a suspension can cause blockages and even aneurysms, which can facilitate rupturing blood vessels and death of cell tissue. When injecting a suspension, it is relatively difficult to obtain uniform particle size to minimize these potential hazards.

Having precipitate in an injectable pharmaceutical composition, increases the chances that the doses given to the host will not be uniform. Furthermore, sterilizing a suspension generally is more difficult than sterilizing a solution. Typically, solutions are easily sterilized by filtration of the solution. A suspension generally requires more extensive and/or expensive sterilization processes, such as separate sterilization of each component.

SUMMARY OF THE INVENTION

The present invention is directed toward a liquid pharmaceutical solution. A solution of the invention includes a substituted pyrimidine, such as trimethoprim, a sulfonamide such as sulfadiazine, an acidic or basic aqueous medium in which the sulfonamide dissolves, such as sodium hydroxide, and a solvent in which the substituted pyrimidine dissolves, such as N-methylpyrrolidone (referred to herein as NMP). These constituents are combined into a composition that constitutes the liquid pharmaceutical solution of the invention. The term "trimethoprim" as used herein refers to 5-[(3,4,5-trimethoxyphenyl)methyl]-2,4-pyrimidinediamine or 2,4-diamino-5-(3,4,5-trimethoxybenzyl)pyrimidine. The term "sulfadiazine" as used herein refers to 4-amino-N-2-pyrimidinylbenzenesulfonamide, 2-sulfanilamidopyrimidine, 2-sulfanilylaminopyrimidine, or sulfapyrimidine. The term "solution" as used herein refers to a clear liquid composition leaving no residue visible to the human eye when filtered through a 0.2 micron filter. Preferably, solutions of the invention are stable. As used herein, the term "stable" refers to a solution that after 24 hours is clear and leaves no residue visible to the human eye when filtered through a 0.2 micron filter.

Preferred solutions of the invention can also include preservatives, such as benzyl alcohol and optionally antioxidants. If benzyl alcohol is present, then preferably it is present in an amount of at least about 0.8 mg/ml of liquid pharmaceutical solution.

An organic solvent, such as N-methylpyrrolidone, in which trimethoprim dissolves is preferably present in the solution in an amount of at least about 40 mg/ml of liquid pharmaceutical solution. Trimethoprim is preferably present in the solution in an amount of at least about 3 mg/ml liquid pharmaceutical solution. Generally, solutions of the invention contain no more than about 5% by weight (i.e., 50 mg/ml) of trimethoprim. A sulfonamide, such as sulfadiazine, is preferably present in an amount of at least about 16 mg/ml of liquid pharmaceutical solution. Generally, preferred solutions of the invention have a 1:5 ratio of trimethoprim to sulfadiazine for an optimal antimicrobial affect in animals. Thus, the amount of sulfadiazine typically will not exceed 25% by weight (i.e., 250 mg/ml). An acidic or basic aqueous medium in which sulfadiazine dissolves, such as sodium hydroxide, is preferably present in an amount of at least 2 mg/ml of liquid pharmaceutical solution. As used herein, the term "organic solvent" refers to a liquid in which a substituted pyrimidine, such as trimethoprim is soluble (i.e., at least 1.5 g/10ml at a temperature not greater than about 45° C.).

Methods for preparing the solution of the invention include dissolving a substituted pyrimidine, such as trimethoprim, in an organic solvent, such as NMP, and dissolving a sulfonamide, such as sulfadiazine, in an acidic or basic aqueous medium, such as sodium hydroxide. There is no particular order required for dissolving the antimicrobial agent(s) and combining them into a solution. Preservatives and antioxidants can also be added to the solution. If a water soluble sulfonamide, such as sodium sulfadiazine, is used, then an acidic or basic aqueous medium generally is not needed to dissolve the sulfonamide. The acidic or basic aqueous medium, which preferably includes aqueous mineral acids or aqueous mineral hydroxides, can be used in many instances to adjust the final pH of the solution.

The invention is also directed toward methods for treating bacterial infections in animals. These methods include: administering to an animal an effective amount of a liquid pharmaceutical solution having trimethoprim, a sulfonamide such as sulfadiazine, an organic solvent, such as NMP, and an acidic or basic aqueous medium in which the sulfonamide dissolves, such as sodium hydroxide. This solution can be administered in any feasible manner. For example, the solution may be injected or administered orally.

DETAILED DESCRIPTION OF THE INVENTION

The invention is directed toward a liquid pharmaceutical solution useful in animals. The solution of the present invention, when administered to animals, is an effective antimicrobial against both gram-positive and gram-negative microorganisms. The liquid pharmaceutical solution provides a uniform dosage. Furthermore, the liquid pharmaceutical solution is less likely to clog needles or to facilitate development of aneurysms because it contains no clumps. The solutions are more easily and uniformly sterilized than suspensions (i.e. compositions not capable of being filtered through a 0.2 micron filter without leaving a residue).

Composition of the Invention

The solution of the invention includes antimicrobial agents, such as a substituted pyrimidine and a sulfonamide, an organic solvent such as NMP, and an acidic or basic aqueous medium in which the sulfonamide dissolves, such as sodium hydroxide.

ANTIMICROBIAL AGENTS

Generally, any pharmaceutical grade antimicrobial agent that dissolves or can be dissolved into solution is useful in the invention. The type of antimicrobial agent used and the potency of the liquid pharmaceutical solution desired can dictate the amount of antimicrobial agent that is used. Applicant has found a substituted pyrimidine, such as omethoprim or trimethoprim, to be an effective antimicrobial agent useful in the invention.

The Merck Index, eleventh edition as published by Merck & Co., Inc., Rahway, N.J. at chemical number 9516 on page 1528, describes trimethoprim as a known antimicrobial agent. Any form of pharmaceutical grade trimethoprim that dissolves in an organic solvent, such as NMP or 2-pyrrolidone, is useful in the invention. Trimethoprim useful in the present invention is commercially available from Sigma Chemical Company in St. Louis, Mo.

Omethoprim is another substituted pyrimidine useful in the invention. Any pharmaceutical grade omethoprim that dissolves in an organic solvent, such as NMP or 2-pyrrolidone, is useful in the invention. For many animal applications, trimethoprim is preferred because of the synergistic antimicrobial effects exhibited when it is combined with a sulfonamide, such as sulfadiazine.

Pharmaceutical grade sulfonamides are also known antimicrobial agents that are useful in the invention. Sodium sulfadiazine, sulfadiazine and sulfamethoxazole are useful sulfonamides in the invention. Because of the synergistic antimicrobial effects in animals with trimethoprim, sodium sulfadiazine or sulfadiazine is preferred for many applications. Any type of pharmaceutical grade sulfadiazine or sodium sulfadiazine that dissolves in an acidic or basic aqueous medium is useful in the present invention. In general, a sulfadiazine that is useful in the invention is commercially available from Sigma Chemical Company in St. Louis, Mo.

Generally, sulfadiazine is soluble in an acidic or basic aqueous medium. By soluble it is meant that at least about 2.3 g/10 ml of sulfadiazine dissolve in the aqueous medium at room temperature. In particular, sulfadiazine is generally soluble in an aqueous mineral acid or aqueous mineral hydroxide solution. Thus, if sulfadiazine is used, it can be dissolved in a sodium hydroxide solution, for example, that is included in the invention. Sodium sulfadiazine is soluble in water. Thus, if sodium sulfadiazine is used in the invention, an acidic or basic aqueous medium may only be needed to adjust the pH of the solution.

The amount of antimicrobial agents useful in the invention varies with the desired potency of the liquid pharmaceutical solution and the type of antimicrobial agent(s) used. Researchers have shown that a 1:5 ratio by weight of a substituted pyrimidine, such as trimethoprim, to a sulfonamide, such as sulfadiazine, is an optimally effective antimicrobial agent. In general, Applicant has found that a stable liquid pharmaceutical solution is obtained when the total amount of antimicrobial agent having trimethoprim and sulfadiazine is not more than about 30% by weight (i.e., 300 mg/ml of liquid pharmaceutical solution). In order to maintain the 1:5 ratio, preferably, the amount of trimethoprim is not greater than about 5% by weight and the amount of sulfadiazine is not greater than about 25% by weight.

In general, the amount of substituted pyrimidine, such as trimethoprim, cannot be so great that it does not dissolve into a solution having an organic solvent, such as NMP therein. The maximum amount of trimethoprim useful in the invention will vary with the amount of other components in the solution. The amount of trimethoprim cannot be so small that the composition is not a sufficiently potent antimicrobial composition.

In preferred embodiments, trimethoprim is present in the liquid pharmaceutical solutions of the invention in an amount not greater than about 50 mg/ml of liquid pharmaceutical solution. More preferably, trimethoprim is present in an amount of at least about 3 mg/ml and not greater than about 40 mg/ml of the liquid pharmaceutical solution.

The amount of sodium sulfadiazine or sulfadiazine included in the solution varies with the desired potency of the antimicrobial composition. The amount of sodium sulfadiazine or sulfadiazine cannot be so great that it does not dissolve, and the amount cannot be so small that the solution is an insufficiently effective antimicrobial. In preferred embodiments, there is not more than 250 mg/ml of sodium sulfadiazine or sulfadiazine in the liquid pharmaceutical solution. In more preferred embodiments, there is at least about 16 mg/ml of sodium sulfadiazine or sulfadiazine and not greater than about 200 mg/ml of sodium sulfadiazine or sulfadiazine.

SOLVENTS USED TO DISSOLVE THE ANTIMICROBIAL AGENTS

Solvents and/or non-neutral mediums are included in the liquid pharmaceutical solution in order to dissolve the antimicrobial agent(s). Typically an organic solvent is used to dissolve the organically soluble antimicrobial agents, such as trimethoprim, included in the liquid pharmaceutical solution. In addition, an acidic or basic aqueous medium is usually included in the solution of the invention to dissolve the acidic or basic aqueous medium soluble antimicrobial agents, such as the sulfonamides. It is noted that if a sodium sulfonamide is used, such as sodium sulfadiazine, an aqueous medium does not need to be acidic or basic because the need to form a salt through use of an acid or base has been accomplished. The solvents and/or aqueous medium used to dissolve the antimicrobial agents should be of pharmaceutical grade and should not interfere with or inhibit the antimicrobial activity of the antimicrobial agents. It is understood that if one type of solvent or aqueous medium is found to dissolve all the antimicrobial agents, then one solvent or aqueous medium can be used.

Applicant has found an acidic or basic aqueous medium-organic solvent co-system to be preferred in the invention, if a substituted pyrimidine, such as trimethoprim, and a sulfonamide, such as sulfadiazine, are the antimicrobial agents used. If a water soluble sulfonamide, such as sodium sulfonamide is used, then an acidic or basic aqueous medium may not be needed to dissolve the sulfonamide.

In order to dissolve the organically soluble antimicrobial agent, such as trimethoprim, Applicant has found that pharmaceutical grade solvent systems containing NMP, polyethylene glycol, 2-pyrrolidone, dimethylacetamide (DMAC), ethanol, propylene glycol, glycofurol and mixtures thereof are useful in the invention. Applicant has found that the amount of antimicrobial agent to be dissolved in the organic solvent may have an effect on which of these solvents should be included in the composition. For example, Applicants found 6 grams of trimethoprim will dissolve in 80 ml of DMAC at room temperature (i.e., about 20° C. to about 25° C.) but that 10 grams of trimethoprim will not dissolve in 80 ml of DMAC at room temperature. Thus, the amount and type of organic solvent used varies with the desired potency of the pharmaceutical solution and the amount of organically soluble antimicrobial agent to be included.

Applicant's preferred solvent system includes NMP and/or 2-pyrrolidone. Applicant found that at room temperature, the solubility of trimethoprim in NMP is about 1.6 g/10 ml. For 2-pyrrolidone, the solubility of trimethoprim at room temperature is about 0.4 g/10 ml. However, at 45° C., the solubility of trimethoprim in 2-pyrrolidone increases to about 2.0 g/10 ml. Because trimethoprim has a greater solubility in NMP at room temperature, NMP is the most preferred organic solvent used in the invention.

Any type of NMP useful in a liquid pharmaceutical solution to dissolve trimethoprim is useful in the present invention. One type of NMP that is useful in the invention is commercially available as 1-methyl-2-pyrrolidinone from Aldrich Chemical Company in Milwaukee, Wis.

The amount of organic solvent in a solution of the invention varies with the amount of substituted pyrimidine, such as trimethoprim, to be dissolved. There must be enough organic solvent to dissolve the substituted pyrimidine. Adding to the composition significantly more organic solvent than is necessary to dissolve the substituted pyrimidine can be economically inefficient. Preferably, if NMP is used, not more than about 645 mg/ml of liquid pharmaceutical solution is added to a solution of the invention. More preferably, at least about 42 mg/ml of the liquid pharmaceutical solution and not greater than about 514 mg/ml of NMP are added to the solution of the invention.

If a water insoluble sulfonamide, such as sulfadiazine, is used as an antimicrobial agent, then any type of pharmaceutical grade acidic or basic aqueous medium that dissolves sulfadiazine in solution is useful in a solution of the invention. In particular, an aqueous mineral acid or aqueous mineral hydroxide can be used. Useful types of aqueous mineral acids include dilute hydrochloric acid, dilute phosphoric acid, or dilute sulfuric acid. If a dilute acid is not used, then the acid could degrade the sulfonamide. Useful types of aqueous mineral hydroxides include sodium hydroxide, potassium hydroxide, or ammonium hydroxide. Sodium hydroxide is most preferred by Applicant. One type of sodium hydroxide that is useful in the invention is commercially available in pellet form from Aldrich Chemical Company in Milwaukee, Wis. as 97% plus ACS reagent grade.

If a water soluble sulfonamide is used as an antimicrobial agent, then an acidic or basic aqueous medium is not needed to dissolve the sulfonamide. These types of media may only be needed to adjust the final pH of the solution. The amount of acidic or basic aqueous medium included in a solution of the invention varies with the amount of sulfonamide to be dissolved and the desired pH of the solution. If the amount of acidic or basic aqueous medium is too small, then all of the sulfonamide will not dissolve into solution. If the amount of acidic or basic aqueous medium is too large, then the solution may be too alkaline or acidic for a liquid pharmaceutical solution. Including more than the necessary amount of acidic or basic aqueous medium in the solution is also economically inefficient.

In more preferred embodiments of the invention, sodium hydroxide is used in whatever amount is needed to dissolve the sulfonamide and obtain a pharmaceutical solution having a pH of at least about 9.0 and not greater than about 11.0. Most preferably, the amount of sodium hydroxide added will be such that the pH of the solution is at least about 9.4 and not greater than about 10.3. Typically, this amount is at least about 2 mg/ml of liquid pharmaceutical solution and not greater than about 40 mg/ml, if an acidic or basic aqueous medium is used to dissolve a sulfonamide in the solution. If an acidic or basic aqueous medium is not used, then enough sodium hydroxide would be added to adjust the pH of the final solution.

OTHER ADDITIVES

Other additives can be included in the liquid pharmaceutical solutions of the invention. These additives include: preservatives, antioxidants, and/or other substances to enhance the stability of the solution. Preservatives help to maintain the sterility and stability of the solution for extended time periods by killing any microorganisms in contact with the solution, so the antimicrobial agent(s) maintain potency. Any type of pharmaceutical grade preservative that is completely soluble in the solutions of the invention is useful. Some examples of preservatives useful in the invention include benzyl alcohol, diethanolamine, chlorocresol, benzethonium chloride, butylparaben, chlorobutanol, metacresol, methylparaben, phenol, myristylgamma, pricolinium chloride, phenylmercuric nitrate, polyparaben or mixtures thereof. Preferably, benzyl alcohol is used because it is readily available, cost effective and has a lower toxicity than other preservatives.

A sufficient amount of preservative is used in order to extend the shelf life of liquid pharmaceutical solutions of the invention by limiting the amount of microorganisms in the solution. If too much preservative is used the solution can become toxic and economically inefficient. If too little preservative is used the solution will not maintain its potency or sterility upon multiple uses for sufficient time periods because it will not be substantially free of microorganisms. Typically, the amount of preservative, such as benzyl alcohol, used is at least about 0.5 mg/ml of liquid pharmaceutical solution and not greater than about 13 mg/ml. This amount can vary with each application because less or more preservative can be added to insure the pH and/or potency of the solution are appropriate for a pharmaceutical solution.

Any pharmaceutical grade antioxidant that dissolves into the solutions of the invention can optionally be used. An antioxidant functions to prevent oxidation of the antimicrobial agent(s) in the presence of oxygen. With significant amounts of oxidation of the antimicrobial agents, the potency of the pharmaceutical solution can decrease. Examples of antioxidants useful in the invention include chlorocresol, ascorbic acid, sodium formaldehyde sulfoxylate, or mixtures thereof.

The amount of antioxidant varies with the amount of oxygen predicted to be in contact with the solution. If too much antioxidant is used in the solution, it can cause the solution to develop an undesirable precipitate. If too little antioxidant is used, then oxygen can significantly oxidize the antimicrobial agent(s) and reduce the potency of the liquid pharmaceutical solution.

In more preferred embodiments of the invention, Applicant does not include an antioxidant in the solution. Applicant reduces the oxygen in the solution by sparging the solution with an inert gas, such as nitrogen, prior to storing the solution. By replacing the oxygen with an inert gas, oxidation of the antimicrobial agents is reduced.

As is obvious in light of the above discussion with respect to aqueous mediums, water is also included in the pharmaceutical solutions of the invention. Any type of water useful for injectable pharmaceutical solutions is useful in the present invention. Preferably, sterile water used for injections is used in the invention. The amount of water to be included varies with the desired dilution of the liquid pharmaceutical solution and with the amount of water needed to dissolve any water soluble compound, such as sodium hydroxide. If there is too little water in the solution, any water soluble compound or sulfonamide will not dissolve. If there is too much water in the solution, then the substituted pyrimidine, such as trimethoprim will precipitate and pharmaceutical potency can be lost.

PROPERTIES OF PHARMACEUTICAL SOLUTIONS OF THE INVENTION

The pharmaceutical solutions of the invention, when stored in a vial at room temperature for at least 5 minutes, preferably for at least 24 hours, more preferably for at least one week, and most preferably for at least one month, remain clear and leave no residue or precipitate visible to the human eye, when filtered through a 0.2 micron filter while maintaining their pH, potency and preservative concentration.

Preferred compositions of the invention remain stable after autoclaving, temperature cycling, and/or storage in natural light. As described in examples below, solutions of the invention can withstand exposure to natural light and days of temperature cycling. The temperature cycling involves: freezing the solution sample for 24 hours at −20° C.; removing the sample from the freezer; viewing the sample for visual changes; allowing the sample to equilibrate to room temperature for 24 hours; putting the sample in an incubator at a temperature of about 50° C.; removing the sample from the incubator; and storing the sample at room temperature for 24 hours. This process was repeated twice with no precipitate forming in the preferred solutions of the invention.

In addition, samples of the solution of the invention were stored next to a window for 24 hours without precipitation. Solutions of the invention can also withstand autoclaving at 120° C. for up to 32 minutes, and accelerated stability tests involving autoclaving the solution at 120° C. and storing them at 110° C. for 10 days. The examples below detail these experiments.

Methods of Making and Using the Invention

In general, a solution of the invention is prepared by dissolving the substituted pyrimidine in an organic solvent, and dissolving the sulfonamide in an acidic or basic aqueous medium, such as sodium hydroxide. As noted previously, if a water soluble sulfonamide, such as a sodium sulfonamide is used, then an acidic or basic aqueous medium is typically not needed, and the sulfonamide can be dissolved in water. The items included in the solution can be combined in any order. For example, trimethoprim can first be dissolved in NMP, and then the dissolved trimethoprim and NMP can be added to a sulfadiazine and sodium hydroxide solution. As a further example, trimethoprim can be dissolved in NMP and added to a sodium hydroxide aqueous solution to which sulfadiazine is subsequently added. Trimethoprim and sulfadiazine can also be added to sodium hydroxide, water and NMP, for example.

In general, the components of the invention are combined to form a liquid pharmaceutical solution. The substituted pyrimidine, sulfonamide, acidic or basic aqueous medium, preservative, organic solvent and optional antioxidant can be added to the solution in any order as long as the sulfonamide and substituted pyrimidine are dissolved. Heat and/or stirring can be used to facilitate full dissolution of the antimicrobial agents.

Preferably, the temperature of the mixture during and after the preparation process does not rise above about 45° C. The preferred maximum temperature depends upon the amount of antimicrobial agents in the mixture. If the temperature of the mixture gets too high during preparation, then the substituted pyrimidine or sulfonamide can thermooxidize. If the temperature of the mixture is too low, then the antimicrobial agents will not quickly dissolve. The addition of an aqueous mineral acid or aqueous mineral hydroxide to the mixture can increase the mixture's temperature. Therefore, the mixture may have to be cooled to avoid significant thermooxidation of the antimicrobial agents. However, the mixture, in accordance with the invention, should not be cooled to a point at which a precipitate forms. Solutions in accordance with the invention can be prepared at room temperature without external heating. Continuous stirring is preferred while all of the components are added to the mixture.

Water, preferably sterilized and useful in injectable solutions, typically is the aqueous medium included in the invention. This water can be used, for example, to dissolve solid compounds included in the invention and/or to bring the solution up to volume for the appropriate antimicrobial potency.

In general, the administration and dosage of solutions of the invention will be guided by the judgment of the health care provider. It is noted that solutions of the invention can be administered orally, intramuscularly, parenterally, subcutaneously, intravenously, buccally, and/or rectally. Preferably, the solutions of the invention are administered orally or by injection.

The dosage administered are typically those dosages prescribed for the antimicrobials used. In particular, the dosages should be such that both gram positive and gram negative bacterial infections can be treated. These types of bacteria include: Streptococci, Staphylococci, *actinobacilli*, *actinomyceae*, Salmonella, Pasteurella, Pneumococci, Proteus, *E. coli*, Corynebacteria, Vibrio, Bordetelle, Brucella, Klebsiellae, and Haemophilae.

While not intending to limit the present invention in any matter, the following examples illustrate in more detail how the compositions of the invention are made and the properties exhibited by the solutions of the invention.

EXAMPLES

Example 1

Preparation of a Trimethoprim/Sulfadiazine Solution

A stable solution of sulfadiazine and trimethoprim was obtained by the following method. Ten milliliters of NMP were put into a beaker. Trimethoprim in an amount of 0.8 grams was added and stirred until the trimethoprim was dissolved. Water for injection was added to the beaker in an amount of 7 ml and stirred. Sodium hydroxide was added to the beaker in an amount of 0.6 grams and stirred. Sulfadiazine in an amount of 4.0 grams was added to the beaker and stirred. No precipitate was observed with the human eye for 11 months, when the solution was stored at room temperature.

Example 2

Preparation of an Injectable Trimethoprim/ Sulfadiazine Solution

An injectable solution of the invention was obtained using the following procedure. NMP in an amount of 50 ml was placed in a 250 ml beaker having a mark at 100 ml and containing a magnetic stirring bar. Trimethoprim was added to the beaker in an amount of 4.0 grams. The mixture was stirred for about 5 minutes to obtain a clear solution. Water for injection in an amount of 35 ml was added to the mixture in the beaker. The mixture remained clear, but the temperature of the mixture rose to about 39° C. Sodium hydroxide pellets in the amount of 3.0 grams were added to the beaker to obtain a turbid mixture. The temperature rose to about 42° C. Sulfadiazine was added to the mixture in an amount of 20.0 grams, and the mixture was stirred to obtain a clear solution. A clear solution was obtained within 10 minutes. The temperature of the solution was 40° C. Benzyl alcohol was added in an amount of 1 gram. The beaker from which the benzyl alcohol was poured was rinsed twice with the solution to which the benzyl alcohol was added, and the rinses were added to the solution. The solution temperature was 36° C. The beaker having the solution therein was immersed in ice water until the solution temperature dropped to 25° C. At this point the pH of the solution was 9.38. A 5 molar solution of sodium hydroxide was added dropwise to adjust the pH to 10.21. This required about 1.3 ml of solution. The solution was brought to volume with water for injection. The final pH of the solution was 10.20. The solution was filtered through a #1 Whatman paper filter commercially available from Whatman, Inc. and stored in an amber vial.

One milliliter of solution of the overall formula included 40 mg of trimethoprim, 200 mg of sulfadiazine, 514 mg of NMP, 30 mg of sodium hydroxide, 10 mg of benzyl alcohol, and water for injection.

Stability tests were conducted on the formulation.

Example 3

Stability Tests of Solution of the Invention

The solution of the invention prepared in Example 2 was stored in 5 vials that were crimped with a rubber stopper and an aluminum overseal. The first vial was a clear glass vial having one-fifth of the solution volume therein and stored at room temperature under air. The second vial was an amber vial having one-fifth of the solution therein and stored at room temperature under air. The third vial was an amber vial having one-fifth of the solution and stored at room temperature under nitrogen. The fourth vial was an amber vial having one-fifth of the solution therein and was subjected to the below detailed temperature cycling process under air. The fifth vial was an amber vial having one-fifth of the solution therein and was subjected to the below detailed temperature cycling process under nitrogen.

The first three vials were placed next to a window and exposed to natural light. After 24 hours, no changes were detected in the solutions contained in vials 1–3. The solution in vial 1, after 24 hours, had turned from clear to a dark brownish-yellow color. However, there was no precipitate visible to the human eye in this vial. The solutions of the invention, because of this results, are preferably stored in amber vials or other appropriate amber storage vessels.

The fourth and fifth vials were placed in a freezer at a temperature of −20° C. After 24 hours, vials 4 and 5 were taken out of the freezer and allowed to equilibrate at room temperature for 24 hours. After this 24 hour equilibrate, no changes were detected in the solution in vials 4 and 5, and these vials were placed in an incubator at 50° C. Twenty-four hours later, vials 4 and 5 were taken out of the incubator and allowed to equilibrate to room temperature for 24 hours. After this 24 hour period, solutions in vials 4 and 5 were placed again in the freezer at −20° C. After 24 hours of being in the freezer temperature, vials 4 and 5 were taken out of the freezer and allowed to equilibrate to room temperature for 24 hours. Vials 4 and 5 were then placed in an incubator at 50° C. After 24 hours, vials 4 and 5 were removed from the incubator and allowed to equilibrate to room temperature. No precipitate or discolorations were observed in vials 4 and 5.

Example 4

Autoclaving Pharmaceutical Solutions

A liquid pharmaceutical solution was prepared as detailed in Example 2. The solution was prepared in a 400 ml beaker marked tat 200 ml. The final pH of the solution was 10.20. Five milliliters of the solution was retained for HPLC studies as described below. The remaining amount of solution was divided into eight equal portions and each portion was put into a 100 ml amber bottle. These bottles were closed with a grey rubber stopper and crimped with an aluminum overseal. Four of the eight bottles were filled with nitrogen before the solution was added. Six of the eight bottles were autoclaved according to the scheme discussed below.

Bottles 1 and 2 were autoclaved for 8 minutes at 120° C. Bottle 1 contained oxygen and bottle 2 was sparged with nitrogen prior to filling with the solution. Bottles 3 and 4 were autoclaved for 16 minutes at 120° C. Bottle 3 contained oxygen and bottle 4 was sparged with nitrogen prior to filling with the solution. Bottles 5 and 6 were autoclaved for 32 minutes at 120° C. Bottle 5 had oxygen in it. Bottle 6 was sparged with nitrogen before filling with the solution. Bottles 7 and 8 were not autoclaved. Bottle 7 contained oxygen and bottle 8 was sparged with nitrogen before filled with the solution.

Discoloration was observed in samples having oxygen therein. Samples having only nitrogen therein were not discolored. They remained the original clear color after autoclaving at 120° C. for 8, 16 and even 32 minutes. Measurements of the pH in all eight solution samples showed no significant changes in pH. Therefore, Applicant believes that in the bottles having air therein, there was some oxidation of the sulfadiazine, but not enough to affect the pH.

Overall, the samples were within +/−2% of the label claims (i.e., +/−2% of the original potency of the antimicrobial agents based on mg/ml). The solutions in the bottles having oxygen therein became discolored, but the antimicrobial agent potency did not seem to decrease. Immediately below is a table of the results of these tests with respect to color, clarity, leakage, precipitation as observed by the human eye, pH and treatment.

| ID# | Color | Clarity | Leakage | Particles | pH | Treatment/ Storage Conditions |
|---|---|---|---|---|---|---|
| Bottle 1 | Dark Yellow | Clear | None | None | 10.16 | Autocl. 8 Minutes |
| Bottle 2 | Yellow | Clear | None | None | 10.18 | Autocl. 8 Minutes Under $N_2$ |
| Bottle 3 | =1 | Clear | None | None | 10.17 | Autocl. 16 Minutes |
| Bottle 4 | =2 | Clear | None | None | 10.18 | Autocl. 16 Minutes Under $N_2$ |
| Bottle 5 | =1 | Clear | None | None | 10.17 | Autocl. 32 Minutes |
| Bottle 6 | =2 | Clear | None | None | 10.18 | Autocl. 32 Minutes Under $N_2$ |
| Bottle 7 | <2 | Clear | None | None | 10.20 | Non-Autocl. |
| Bottle 8 | <7 | Clear | None | None | 10.20 | Non-Autocl. Under $N_2$ |

\>: Darker Than
<: Lighter Than
=: Same As

Example 5

Accelerated Stability Testing of the Solutions

A solution of the invention was prepared in accordance with the detailed method in Example 2. The solution was divided into 5 separate vials. All of the vials were incubated or stored in 110° C. for 10 days. The first vial contained oxygen and before being stored at 110° C. for 10 days, was autoclaved for 32 minutes under air having oxygen therein. The second vial, which also was stored at 110° C. for 10 days, was previously autoclaved for 32 minutes under nitrogen. The third vial was not autoclaved, and it was stored at 110° C. for 10 days under oxygen. The fourth vial was not autoclaved and it was stored at 110° C. for 10 days under nitrogen. The fifth vial was autoclaved for 16 minutes under nitrogen and it was not stored at 110° C. for 10 days. It was stored at room temperature for 10 days. The bottles that contained oxygen caused discoloration of the solution and a drop in pH with formation of minute particles. The samples stored under nitrogen, whether autoclaved or not, did not show change in the pH or display discoloration. The table below summarizes the results.

| ID# | Color | Clarity | Leakage | Particles | pH | Treatment | Storage |
|---|---|---|---|---|---|---|---|
| C1-$O_2$ | Dark Reddish Brown | Not Clear | OK | Few–Small | 9.83 | Autocl. 32 Minutes - $O_2$ | 10 days at 110° C. |
| C2-$N_2$ | Reddish Brown | Clear | OK | None | 10.23 | Autocl. 32 Minutes - $N_2$ | 10 days at 110° C. |
| D1-$O_2$ | Same as C1-$O_2$ | Not Clear | OK | Few–Small | 9.85 | Non-autocl. - $O_2$ | 10 days at 110° C. |
| D2-$N_2$ | Lighter than C2-$N_2$ | Clear | OK | None | 10.16 | Non-Autocl. - $N_2$ | 10 days at 110° C. |
| B2-$N_2$ | Yellow- Reddish | Clear | | None | 10.10 | Autocl. 16 Minutes - $N_2$ | Room Temp. |

The samples having nitrogen therein did not exhibit a pH change. All of the samples exhibited a drop in potency of less than 5% of the label claim as measured by HPLC( i.e., high performance liquid chromatography), pursuant to the following procedure.

Assay of Trimethoprim and Sulfadiazine

The procedure required the following materials and/or equipment: HPLC grade water; analytical balance (calibrated); acetonitrile (HPLC grade); 10, 25 and 50 ml volumetric flasks; a vacuum drying oven; sulfuric acid (ACS reagent grade); 200–1000 μl pipettor and tips; HPLC system (Isocratic HPLC System With Autosampler and Integrator); Dimethylformamide (HPLC grade); 8 ml volumetric pipettes; UV detector at 254 nm; USP Trimethoprim Reference Standard; Autosampler glass vials (1.5–2.0 ml), caps and septa; Desiccator; USP Sulfadiazine Reference Standard; 3 ml plastic disposable syringes; 0.45 μm syringe filters; Glass vials (about 20 ml); BDS Hypersil C8 5 μm column (250×4.6 mm).

The Mobile Phase Preparation was performed as follows. concentrated H2SO4 in an amount of 5.56 ml (1.39 ml/liter) were pipetted into 4000 ml of HPLC water and mixed. This solution in an amount of 3,520 ml (88 parts) were mixed with 480 ml (12 parts) of HPLC acetonitrile. The mobile phase was then degassed.

The Preparation of Standards was performed as follows. A portion of USP-Sulfadiazine was dried for 2 hours at 105° C. The vial that contained the sulfadiazine was promptly capped tightly after the vial was removed from the oven, and the vial was stored in the desiccator until weighed. These samples were weighed out on the same day that the standard was dried. Dried sulfadiazine in an amount of 80.64 mg was weighed and put into glass vials and the weights recorded. This weighed standard was stored, tightly capped and protected from light, until it was needed for assay.

A Portion of USP-Trimethoprim was dried for 4 hours at 105° C. in a vacuum (i.e., less than 20 mm Hg). Dried trimethoprim in an amount of 40.98 mg was weighed and stored in separate containers as detailed above with respect to the sulfadiazine.

The sulfadiazine standard containing 80.64 grams of dried sulfadiazine was then dissolved in 2 to 3 ml of dimethylformamide (DMF). The solution was quantitatively transferred to a 10 ml volumetric flask. The vial was rinsed three times with DMF and the rinses were added to the volumetric flask. The solution was brought to volume with DMF, capped, and mixed by inverting at least 15 times. This became the sulfadiazine stock solution.

The 40.98 mg of dried trimethoprim were then dissolved in 2 to 3 ml of DMF, and then quantitatively transferred to a 25 ml volumetric with at least 3 additional rinses of DMF. The solution was mixed by inverting at least 15 times. This became the trimethoprim stock solution.

Using 8 ml volumetric pipettes, 8 ml of the sulfadiazine stock solution were mixed with 8 ml of the trimethoprim stock solution to give a sulfadiazine/trimethoprim stock solution of about 4.0/0.8 mg/ml.

Dilutions of the sulfadiazine/trimethoprim stock solution were made by pipetting the amounts shown below into 50 ml volumetric flasks using an adjustable pipettor.

| Standard | Approximate SDZ/TMP Concentration (ug/ml) | Volume of SDZ/TMP Stock Solution (ml) |
|---|---|---|
| S1 | 20.0/4.0 | 0.25 |
| S2 | 30.0/6.0 | 0.375 |
| S3 | 40.0/8.0 | 0.5 |
| S4 | 50.0/10.0 | 0.625 |
| S5 | 60.0/12.0 | 0.75 |

The solution was then brought to volume with the HPLC mobile phase, capped and mixed by inverting at least 15 times. A Control Blank sample was prepared consisting of HPLC mobile phase to run as part of the standard curve. The standards and the mobile phase Control Blank were filtered through 0.45 μm syringe filters into autosampler vials. The vials were capped and labeled. An extra vial of the S3 standard was filtered for use in system suitability testing. The standards were then ready for HPLC analysis.

The Sample Preparation was as follows. Two samples from each bottle of the solution to be assayed were prepared to be assayed. A 1.0 ml sample was transferred (using a 200–1000 μl adjustable pipettor) into each of the 50 ml volumetric flasks. In the fume hood, the flasks were brought to volume with DMF, capped and mixed by inverting at least 15 times. DMF solution was transferred in an amount of 0.5 ml from each flask to a clean 50 ml volumetric flask, using the same 200–1000 μl adjustable pipettor used to make the standard curve dilutions. The flasks were brought to volume with the HPLC mobile phase, capped and mixed by inverting at least 15 times. Each dilution was filtered through a 0.45 μm syringe filter into autosampler vials, capped and labelled. The samples were then ready for HPLC analysis.

The HPLC system consisted of a pump, UV detector and autosampler. Data was collected by a computerized data system. The HPLC conditions were:

Mobile Phase: 12% acetonitrile, 88% 25 mM $H_2SO_4$. Prepared by mixing 12 parts of HPLC grade acetonitrile with 88 parts of 25 mM $H_2SO_4$ (made by mixing 1.39 ml of concentrated $H_2SO_4$ with 1 liter of HPLC grade water). Degassing was performed.

Wavelength: 254 nm

Flow Rate: 1.5 ml/min

Injection Volume: 40 μl

Column: BDS Hypersil C8, 5 μm, 250×4.6 mm

Run Time: 11 minutes (programmed on the data system). The autosampler was programmed to allow sufficient time for saving or printing the chromatograms.

Retention Time: Under these conditions, sulfadiazine eluted at about 3–4 minutes, and trimethoprim at about 7.5–9.5 minutes.

The system suitability check was performed as follows. At the beginning of each run, the system was checked as follows. Five (5) injections of the S3 standard were made. The CV of each of the sulfadiazine and trimethoprim peak areas was less than 2.0%. On one of the chromatograms, the tailing factors (T) for the sulfadiazine and trimethoprim peaks were calculated as follows:

$$T = W_{0.05}/2f$$

Where "$W_{0.05}$" is the peak width at 5% of the peak height and "f" is the distance from the leading edge of the peak to the peak maximum. The tailing factor must be 1.5 or less. Each peak needed to be printed separately on a magnified scale in order to make accurate measurements. If the tailing factor was greater than 1.5, the system failed the test and was not used for this assay until the proper adjustments had been made and the system passed the test.

The resolution (R) between sulfadiazine and trimethoprim were calculated as follows:

$$R = (t_2 - t_1)/\tfrac{1}{2}(W_1 + W_2)$$

where "t" and "W" represent retention times and baseline band widths, respectively, for the sulfadiazine and trimethoprim peaks. The baseline band width is the width of a peak measured by extrapolating the relatively straight sides to the baseline.

If the resolution was less than 15, the system failed and the test was not used for this assay until proper adjustments were made and the system passed the test.

The sample injections were performed as follows. Duplicate injections were made for each sample, standard and control blank. The S3 standard was reanalyzed at least once every 20 sample injections to verify that the system performance had not changed over time. The expected peak areas for sulfadiazine and trimethoprim were ±5% of the peak areas measured in the initial analyses of this standard.

The concentration of sulfadiazine and trimethoprim in each standard were calculated using the following equation:

$$Concentration\ (\mu g/ml) = W \div Vd \div 2 \times (Vp/Vm) \times 1000\ \mu g/ml$$

Where "W" is the weight of sulfadiazine or trimethoprim standard in mg. "Vd" is the volume of DMF solution in which the sulfadiazine or trimethoprim was dissolved (10 ml for sulfadiazine, 25 ml for trimethoprim). "Vp" is the volume of sulfadiazine/trimethoprim stock solution pipetted into the volumetric flask (0.25, 0.375, 0.5, 0.625, or 0.75 ml). "Vm" is the volume of mobile phase solution in which the stock solution was diluted (50 ml).

For both the sulfadiazine and the trimethoprim, a six point standard curve was prepared (Control Blank plus 5 concentrations of drug) by plotting the drug concentration on the x-axis versus the HPLC peak area on the y-axis. The line of best fit was then determined for each of the standard curves by least squares linear regression analysis. The correlation coefficient for each standard curve was >0.99 in order to be considered acceptable. Using the linear regression equations, the concentration of sulfadiazine and trimethoprim were calculated in each unknown sample by inserting the measured peak area into the equation and solving for concentration (in μg/ml). The μg/ml concentrations in each injected sample were then converted to mg drug per ml of solution that was assayed using the following equation:

$$mg\ drug/ml\ of\ solution\ to\ be\ assayed = Conc\ (\mu g/ml) \times DF \times Volume\ (ml) \div 1000\ \mu g/mg \div Solution\ Vol.(ml)$$

Where "Conc (μg/ml)" is the μg/ml concentration of sulfadiazine or trimethoprim calculated from the standard curve equation as described above. "DF" is the dilution factor for the dilution step (DMF solution diluted in HPLC mobile phase =100). "Volume" is the volume of DMF used to dissolve the solution to be assayed (50 ml). "Solution Vol." is the volume of the solution to be assayed that was dissolved in the DMF.

The mg drug/ml of the solution to be assayed was converted to percent of label claim by dividing the mg/ml figure by the label claim and multiplying by 100.

The above-identified formulation in this example is stable as long as most of the air is excluded from the storage vial.

When significant amounts of air are in the vial, oxidation of the sulfadiazine and trimethoprim occurs due to the presence of oxygen. Use of antioxidants can minimize this oxidation, but antioxidants that do not precipitate the other components of the solution must be used. Removal of air from the vials also decreases the amount of carbon dioxide in the vial. Carbon dioxide tends to decrease the solubility of the sodium sulfadiazine by converting it to the insoluble free sulfadiazine. In order to decrease the amount of air in the vials, the solution can be sparged with nitrogen prior to aseptic filtration, and/or the vials can be filled with nitrogen prior to or after filling.

Example 6

Use of Ascorbic Acid as an Antioxidant

Trimethoprim in an amount of 4.0 grams was dissolved in 50 ml of NMP. Water for injection in an amount of 31 ml was added to the mixture. Sodium hydroxide in an amount of 3.0 grams was added to the mixture. Sulfadiazine in an amount of 20 grams was added to the mixture. A substantially clear solution was obtained, but a few particles were left undissolved. Benzyl alcohol in an amount of 1.0 gram was then added to the mixture. Ascorbic acid in an amount of 40 mg was dissolved in 1 ml of water for injection and the solution was added dropwise to the mixture. The beaker was rinsed with 1 ml of water for injection and then with 1 ml of the mixture and these rinses were added to the flask. A clear solution was obtained. The pH of the solution was 9.45 and was adjusted to 10.29 with 5 Molar sodium hydroxide (i.e., about 1.1 ml were needed to adjust the pH). The beaker was then cooled to 24° C. The solution was transferred to a 100 ml graduated cylinder. The volume of the solution was 98 ml. Two milliliters of water for injection were added to take the solution to volume. The final pH was 10.29. The solution was filtered through a #1 Whatman paper filter and stored in two amber vials. The #1 amber vial was stored under oxygen and the #2 amber vial was stored under nitrogen. After 24 hours, the solution contained dust-like particles in both vials.

Example 7

Use of Chlorocresol as Antioxidant and/or Preservative

The solution of the invention was prepared in accordance with Example 6 with the exception that benzyl alcohol and ascorbic acid were replaced with chlorocresol.

Trimethoprim in an amount of 4.0 grams was dissolved in 50 ml of NMP. Water for injection in an amount of 31 ml was added to the mixture. Sodium hydroxide in an amount of 3.0 grams was added to the mixture. Chlorocresol (4-chloro-3-methylphenol from Aldrich) in an amount of 100 mg was dissolved in a small beaker with 1 ml of water for injection and 0.5 ml 5 Molar sodium hydroxide solution. This solution was added to the mixture. The small beaker was rinsed with 1 ml of water for injection and the rinse was added to the mixture. Everything was dissolved, the temperature of the solution was 31° C. and the pH was 9.67. The pH was adjusted to 10.26 with the addition of 5 Molar sodium hydroxide solution (0.6 ml was used), and the temperature decreased to 30° C. The solution was then cooled to 25° C., transferred to a 100 ml graduated cylinder (volume was 98 ml) and with the addition of 2 ml of water for injection, the solution was brought to volume. The pH of the solution was 10.25. The solution was then filtered through a #1 Whatman paper filter and stored in two amber vials. The first vial was stored under air having oxygen therein, and the second amber vial was stored under nitrogen. After 24 hours, the solution was still clear.

Example 8

Use of Sodium Formaldehyde Sulfoxylate as Antioxidant

The solution of the invention was prepared in accordance with Example 6 with the exception that sodium formaldehyde sulfoxylate was used as an antioxidant. Instead of the ascorbic acid used in the formulation of Example 7 100 mg of sodium formaldehyde sulfoxylate was used. The pH of the solution was 10.28. The solution was filtered through a #1 Whatman paper filter and stored into two amber vials. The first amber vial was stored under air having oxygen therein, and the second amber vial was stored under nitrogen. After 72 hours, the solution was still clear.

Example 9

Stability Studies of a Formulation Having Sodium Formaldehyde Sulfoxylate Therein Seven hundred milliliters of the solution were prepared as follows. NMP in an amount of 350 ml was placed in a 1L beaker equipped with a magnetic stirrer. Trimethoprim in an amount of 28 grams was added to the NMP. A clear solution was obtained within 5 minutes. Water for injection in an amount of 217 ml was added to the mixture. The temperature was 42° C. and then it dropped to 40° C. after stirring for two minutes. Sodium hydroxide in an amount of 21 grams were added to the mixture. The temperature of the mixture was 44° C. Sulfadiazine in an amount of 140 grams were added to the mixture. A clear solution containing some particles was obtained. The temperature decreased to 42° C. Benzyl alcohol in an amount of seven grams was added to the mixture from a 10 ml beaker. This beaker was rinsed twice with solution from the large beaker, and the rinses were added to the mixture. Sodium formaldehyde sulfoxylate in an amount of 700 mg were dissolved in 7 ml of water for injection in a small beaker and added to the mixture dropwise. The small beaker was rinsed with 7 ml of water for injection, and the rinse was added to the mixture. The solution was clear (i.e., no particles). The solution temperature was 39° C., and the pH was 9.34. The pH was adjusted to 10.25 with the addition of 5 Molar sodium hydroxide (about 9.1 ml were used), and the temperature decreased to 36° C. The beaker was immersed in an ice-bath to reduce the temperature to 24° C. The solution was then transferred to a 1L graduated cylinder. The solution volume was 695 ml, and the solution volume was brought to a 700 ml volume with 5 ml of water for injection. The pH of the final solution was 10.23. The solution was filtered through a #1 Whatman paper filter and stored in vials (35 ml per vial) labelled as follows:

| Vial | Stored Under | Type of Studies |
| --- | --- | --- |
| #1-clear glass | Air | Light Stability |
| #2-clear glass | Nitrogen | Light Stability |
| #3-Amber | Air | Accelerated Stability |
| #4-Amber | Air | Accelerated Stability |
| #5-Amber | Nitrogen | Accelerated Stability |
| #6-Amber | Nitrogen | Accelerated Stability |
| #7-Amber | Air | Temperature Cycling |
| #8-Amber | Nitrogen | Temperature Cycling |

-continued

| Vial | Stored Under | Type of Studies |
|---|---|---|
| #9-Amber | Air | Autoclaving and Accelerated Stability |
| #10-Amber | Air | Autoclaving and Accelerated Stability |
| #11-Amber | Nitrogen | Autoclaving and Accelerated Stability |
| #12-Amber | Nitrogen | Autoclaving and Accelerated Stability |

The remaining solution was stored in amber vials, except for 140 ml which was used for an unrelated stopper study. Vials #1 and #2 (in clear glass) and #17 (stored under oxygen) and #18 (stored under nitrogen) in amber glass (obtained from the remaining solution) were placed next to a window where they were exposed to natural light. The initial color of the solution was pale yellow. After eight months: vial #1 had turned a reddish brown color and contained a few small particles visible to the human eye; vial #2 had no discoloration and contained no precipitate; vial #17, which had oxygen therein, had discolored but contained no precipitate; and vial #18, which was sparged with nitrogen, had no discoloration and contained no precipitate.

Vials 9, 10, 11, 12, 19 and 20 were autoclaved at 120° C. for 32 minutes. Vials 19 and 20 were obtained from the remaining solution and were stored under nitrogen. The autoclave was opened when the temperature was 60° C. All of the vials were clear while at 60° C. and after cooling to room temperature.

Example 10

Effect of Temperature Cycling on the Stability of the Injectable Solution

Vials 7 and 8 from Example 9 were placed in the freezer at −20° C. After twenty-four hours, the vials were taken out of the freezer. A small amount of precipitate was observed in both vials. This precipitate re-dissolved upon running the vial under warm water and shaking the vial.

The vials were then placed in an incubator at 50° C. after 24 hours at room temperature.

The vials were taken out of the incubator after 24 hours at 50° C. Vial 7 contained some (about 10) very small particles. Vial 8 was clear without particles.

After 24 hours the vials were placed in the freezer at −20° C.

The vials were taken out of the freezer after 24 hours at −20° C. A few small particles were observed in both vials. In vial 8 the particles re-dissolved upon heating and shaking.

After 24 hours, the vials were then placed in the incubator at 50° C.

The vials were taken out of the incubator after 24 hours at 50° C. Vial 7 contained some small particles which did not re-dissolve upon heating and shaking. Vial 8 did not contain any visible particles.

In conclusion, vial 8 under nitrogen appeared to withstand the temperature cycling better than that filled under air.

Example 11

Accelerated Stability Studies

The following vials from Example 9 were autoclaved for 32 minutes at 120° C. and placed in an oven at 110° C. in the upright or inverted position as indicated:

| #4 | Non-autoclaved | (upright position) |
|---|---|---|
| #6 | Non-autoclaved | (upright position) |
| #10 | Autoclaved | (upright position) |
| #19 | Autoclaved | (inverted position) |
| #12 | Autoclaved | (upright position) |
| #20 | Autoclaved | (inverted position) |

After 24 hours, all vials stored under nitrogen looked clear with no noticeable color change, whereas those stored under air showed some precipitate and discoloration.

After 10 days, the vials were removed from the oven. All vials contained some precipitate. The vials under nitrogen showed a clear (see-through) solution. Those under air showed a dark, reddish solution.

What is claimed is:

1. A stable liquid pharmaceutical solution comprising:
   about 3 to about 50 mg trimethoprim per ml liquid pharmaceutical solution, about 16 to about 250 mg sulfadiazine per ml liquid pharmaceutical solution, about 42 to about 645 mg N-methylpyrrolidone per ml liquid pharmaceutical solution, and a remainder of an acidic or basic aqueous medium.

2. The solution of claim 1, further comprising a preservative.

3. The solution of claim 1, further comprising an antioxidant.

4. A liquid pharmaceutical solution comprising:
   (a) trimethoprim in an amount of at least about 3 mg/ml of liquid pharmaceutical solution;
   (b) sulfadiazine in an amount of at least about 16 mg/ml of liquid pharmaceutical solution;
   (c) N-methylpyrrolidone in an amount of at least about 42 mg/ml of liquid pharmaceutical solution;
   (d) sodium hydroxide in an amount of at least about 2 mg/ml liquid pharmaceutical solution; and
   (e) water in an amount to complete the solution.

5. The solution of claim 4, further comprising benzyl alcohol in an amount of at least about 0.8 mg/ml of liquid pharmaceutical solution.

6. A method of preparing a stable liquid pharmaceutical solution, the method comprising:
   combining in any order about 3 to about 50 mg trimethoprim per ml liquid pharmaceutical solution, about 42 to about 645 mg N-methylpyrrolidone per ml liquid pharmaceutical solution, about 16 to about 250 mg sulfadiazine per ml liquid pharmaceutical solution, and a remainder of an acidic or basic aqueous medium to form a stable liquid pharmaceutical solution.

7. The method of claim 6, further comprising combining a preservative to form a liquid pharmaceutical solution.

8. A method for treating a bacterial infection in an animal comprising:
   (a) administering to the animal a stable liquid pharmaceutical solution in an amount effective to treat the bacterial infection; wherein the stable liquid pharmaceutical solution comprises:

about 3 to about 50 mg trimethoprim per ml liquid pharmaceutical solution, about 16 to about 250 mg sulfadiazine per ml liquid pharmaceutical solution, about 42 to about 645 mg N-methylpyrrolidone per ml liquid pharmaceutical solution, and a remainder of an acidic or basic aqueous medium.

9. The method of claim 8, wherein administering includes orally administering the solution to the animal.

10. A method of preparing a stable liquid pharmaceutical solution, the method comprising:

combining in any order about 3 to about 50 mg trimethoprim per ml liquid pharmaceutical solution, about 42 to about 645 mg N-methylpyrrolidone per ml liquid pharmaceutical solution, about 16 to about 250 mg sodium sulfadiazine per ml liquid pharmaceutical solution, and a remainder of water to form a stable liquid pharmaceutical solution.

* * * * *